(12) United States Patent
Jarrell

(10) Patent No.: US 8,642,952 B2
(45) Date of Patent: Feb. 4, 2014

(54) APPARATUS AND METHODS FOR GAS CHROMATOGRAPHY-MASS SPECTROMETRY

(75) Inventor: Joseph A. Jarrell, Newton Highlands, MA (US)

(73) Assignee: Waters Technologies Corporation, Milford, MA (US)

( * ) Notice: Subject to any disclaimer, the term of this patent is extended or adjusted under 35 U.S.C. 154(b) by 142 days.

(21) Appl. No.: 12/939,571

(22) Filed: Nov. 4, 2010

(65) Prior Publication Data

US 2011/0266433 A1 Nov. 3, 2011

Related U.S. Application Data

(60) Provisional application No. 61/259,687, filed on Nov. 10, 2009.

(51) Int. Cl.
*H01J 49/16* (2006.01)

(52) U.S. Cl.
CPC .................................. *H01J 49/168* (2013.01)
USPC ....................................................... 250/288

(58) Field of Classification Search
USPC ....................................................... 250/288
See application file for complete search history.

(56) References Cited

U.S. PATENT DOCUMENTS

| | | | |
|---|---|---|---|
| 5,175,431 A | 12/1992 | Eisele et al. | |
| 5,869,344 A * | 2/1999 | Linforth et al. | 436/173 |
| 6,534,765 B1 * | 3/2003 | Robb et al. | 250/288 |
| 6,825,926 B2 * | 11/2004 | Turner et al. | 356/244 |
| 6,992,299 B2 | 1/2006 | Lee et al. | |
| 7,520,920 B1 * | 4/2009 | Gregory et al. | 96/106 |

FOREIGN PATENT DOCUMENTS

WO 2006/060130 6/2006

OTHER PUBLICATIONS

Keller, et al; Gasdynamic focusing for sample concentration in ultrasensitive analysis; Applied Optics, vol. 23, No. 13, Jul. 1, 1984, pp. 2146-2151.
Stiller, et al; Supersonic Jet Spectroscopy with a Capillary Gas Chromatographic Inlet; Anal. Chem. 1987, vol. 59, pp. 567-572.
McEwen, et al; A Combination Atmospheric Pressure LC/MS:GC/MS Ion Source: Advantages of Dual AP-LC/.MS: GC/MS Instrumentation; 2005 American Society for Mass Spectrometry, J. Am. Soc. Mass Spectrom. vol. 16, pp. 1730-1737.
Luosujarvi, et al.; Gas chromatography/mass spectrometry of polychlorinated biphenyls using atmospheric pressure chemical ionization and atmospheric pressure photoionization microchips; Rapid Commun. Mass Spectrom. 2008, vol. 22, pp. 425-431.
Schiewek, et al; Development of a multipurpose ion source for LC-MS and GC-API MS; Anal. Bioanal. Chem. 2008, vol. 392, pp. 87-96.
Horning, et al; Development and Use of Analytical Systems Based on Mass Spectrometry; Clinical Chemistry, vol. 23, No. 1, 1977, pp. 13-21.
Zhou, et al; Incorporation of a Venturi Device in Electrospray Ionization; Anal. Chem. 2003, vol. 75, pp. 5978-5983.

\* cited by examiner

*Primary Examiner* — Jack Berman
*Assistant Examiner* — Eliza Osenbaugh-Stewart
(74) *Attorney, Agent, or Firm* — Muirhead and Saturnelli, LLC

(57) ABSTRACT

The invention provides improved apparatus for, and methods of, ionizing analyte molecules in a flow of gas, typically at or around atmospheric pressure. The invention may be used to facilitate mass spectrometric analysis of analytes comprised in the effluent form a gas chromatograph. Ionization may be effected by atmospheric pressure chemical ionization or by atmospheric pressure photo ionization.

23 Claims, 5 Drawing Sheets

APPARATUS AND METHODS FOR GAS
CHROMATOGRAPHY-MASS
SPECTROMETRY

CROSS REFERENCE TO RELATED APPLICATIONS

This application claims benefit of U.S. Provisional Application No. 61/259,687, filed Nov. 10, 2009. The contents of this application is expressly incorporated herein by reference in its entirety.

FIELD OF INVENTION

This invention relates to apparatus and methods for mass spectrometrically analysing analyte materials comprised in a flow of gas, for example in the effluent from a gas chromatograph, typically at or slightly above atmospheric pressure.

BACKGROUND

Gas Chromatography—Mass Spectrometry (GCMS) is a powerful analytical technique first commercially developed in the late 1960's but which has to some extent been eclipsed by the more recent development of liquid chromatography-mass spectrometry as a routine analytical tool. Nevertheless, in view of its high sensitivity and relative ease of use, GCMS is a valuable method of analysis of compounds amenable to separation by gas chromatography.

Many prior GCMS instruments employ ionization sources operable at sub-atmospheric pressure, for example electron impact or chemical ionization sources in which ionization of analyte molecules takes place at a pressure typically less than about 2 torr. At least in the case of packed column gas chromatography where a carrier gas flow rate of more than about 5 ml/minute is employed, a mass-selective separation device such as a jet separator is typically employed. This selectively removes the low mass carrier gas (typically helium) from the column effluent while transmitting a greater proportion of the higher mass analyte molecules in a reduced flow which the mass spectrometer can tolerate. Alternatively, in the case of capillary column gas chromatography, where a flow rate of less than 1 or 2 ml/minute is usually employed, the effluent from the column may be conveyed directly into the ion source of the spectrometer through a capillary restrictor, frequently the chromatographic column itself. If necessary a simple flow splitter may be used if the column flow rate is too great.

In most cases, the separator, capillary restrictor and all other components of the transfer system are heated to minimise analyte losses by condensation.

If a separator or flow splitter is employed, substantial loss of sample is inevitable. Further, the ionization processes involved in electron impact and (to a lesser extent) in chemical ionization sources are relatively violent and often result in excessive fragmentation of labile analytes, even those which can be successfully separated by gas chromatography. Experience with the use of atmospheric pressure ionization sources in liquid chromatography—mass spectrometry has shown that such sources induce far less fragmentation, so their use for GCMS is an attractive proposition, both from the standpoint of lower fragmentation and the lack of any flow splitting requirement. However, despite reports describing such sources first appearing in the 1970's, the technique has not so far met expectations, particularly in respect of sensitivity.

OBJECT OF THE INVENTION

An object of the invention is to provide improved atmospheric pressure ionization apparatus for generating ions from an analyte comprised in a flow of gas, typically the effluent from a gas chromatographic column but also including that from supercritical fluid chromatography source. Another object is to provide improved mass spectrometers for analysing analytes comprised in a flow of gas, typically the effluent from a gas chromatographic column. A third object is to provide improved gas chromatograph-mass spectrometers.

Further objects of the invention are to provide improved methods of ionizing at atmospheric pressure analytes comprised in a flow of gas, typically the effluent from a gas chromatographic column, and to provide improved methods of mass spectrometrically analysing analytes comprised in a flow of gas, typically the effluent from a gas chromatographic column but also including that from supercritical fluid chromatography source. A yet further objective of the invention is to provide improved methods of analysis by gas chromatography-mass spectrometry.

SUMMARY OF THE INVENTION

An embodiment of the invention may provide apparatus for ionizing analyte molecules comprised in a flow of a first gas, said apparatus comprising:
 a) an inlet tube having a first exit through which said first gas may be discharged into an ionization region downstream of said exit at a first linear velocity;
 b) a sheath tube disposed around said inlet tube to define a substantially annular space between the exterior of said inlet tube and the interior of said sheath tube, said sheath tube comprising a second exit downstream of said first exit,
 c) means for causing a flow of a second gas to flow through said substantially annular space through said second exit at a second linear velocity, higher than said first linear velocity; and
 d) means for ionizing at least some of said analyte molecules in said ionization region;
wherein, downstream of said first exit, said sheath tube narrows to direct the flow of said second gas around said ionization region and to limit its volume.

By directing the flow of second gas as described, the ionization volume is reduced from that which it would occupy in the absence of the second gas, thereby increasing the concentration of analyte molecules in the space where they can effectively be ionized, so that the number of analyte ions generated is increased.

Preferably, both the inlet tube and capillary tube have circular cross sections and are concentrically disposed. However, tubes of any cross-sectional shape can be used. In certain embodiments the sheath tube is formed so that its cross sectional area decreases steadily beyond the first exit (of the inlet tube) so that the flow of the second gas as it leaves the second exit is directed towards the axis of the tubes. Without being limited by theory it is believed that because the linear flow velocity of the second gas is greater than that of the first gas, an aerodynamic focusing effect is exerted on the flow of the first gas, limiting the volume which it occupies as it is discharged from the first exit.

In other embodiments, the first gas is discharged into the ionization region at a pressure greater than 300 torr, preferably between about 650 and 850 torr. The first gas may be any gas suitable for carrying an analyte and may comprise binary gases and gases near or around exceeding the critical temperature and pressure. The means for ionizing comprise any manner of ionization including, charged inlet tubes, a corona discharge and the like. In further embodiments the first gas is discharged into the ionization region at approximately atmospheric pressure. Analyte molecules are ionized by atmospheric pressure chemical ionization (APCI) processes, typically but not necessarily exclusively by reaction with ionized species generated from the second gas in a corona discharge. In some embodiments the corona discharge is generated using an electrode positioned downstream of both the first and second exits. In another embodiment the corona discharge is generated using an electrode disposed upstream of the first exit in the space between the inlet tube and sheath tube through which the second gas is flowing. In such a case, charged species is generated in the second gas and carried into the ionization region by the flow of second gas where they react with analyte molecules to generate analyte ions.

Analyte molecules are alternatively be ionized by atmospheric pressure photoionization (APPI). In this embodiment, a beam of photons, typically from a UV lamp or laser, is disposed to intersect the ionization region and to ionize at least some analyte molecules therein.

In other embodiments, the apparatus further comprise a gas chromatograph, the effluent from which is the first gas. Preferably, the inlet tube comprises a capillary, which is an extension of the gas chromatographic column itself. The sheath tube and/or second gas is preferably heated in order to minimize analyte loss through condensation or absorption in the inlet tube. Preferably, the apparatus comprise a mass spectrometer having an entrance orifice disposed to receive ions formed in the ionization region. The efficiency of ion collection and the transmission of ions through the entrance orifice is increased when the volume of the ionization region is minimized by the aerodynamic focusing action of the second gas.

Viewed from another aspect, a further embodying of the invention comprise a method of ionizing analyte molecules in a flow of a first gas, said method comprising:

a) passing said first gas through an inlet tube having a first exit and discharging it at a first linear velocity through said first exit into an ionization region downstream of said first exit;

b) passing a second gas through a substantially annular space between the exterior of said inlet tube and the interior of a sheath tube having a second exit and which is disposed around said inlet tube, and discharging said second gas at a second linear velocity, greater than said first linear velocity, through said second exit downstream of said first exit; and c) ionizing at least some of said analyte molecules in said ionization region;

wherein said second gas is directed through said second exit towards the axis of said sheath tube to surround said ionization region and to limit its volume.

Preferably, the first gas is discharged into the ionization region at a pressure greater than 300 torr, and, move preferably, between about 650 and 850 torr.

The means for ionizing is any manner of ionization, including charged inlet tubes, corona discharge and the like. In further embodiments, the first gas is discharged into the ionization region at approximately atmospheric pressure. Analyte molecules may be ionized by atmospheric pressure chemical ionization (APCI) processes, typically but not necessarily exclusively by reaction with ionized species generated from the second gas in a corona discharge. Analyte molecules may also be photoionized by use of UV radiation from a lamp or laser.

Other methods according to the invention comprise introducing analyte molecules into the first gas (for example, helium) and passing the resultant gas through a gas chromatographic column to separate in time different analyte molecules, and thence into the inlet tube. Ions generated in the ionization region is passed into a mass spectrometer for mass analysis.

The second gas used in methods and apparatus according to the invention may be an inert gas such as nitrogen or argon.

DETAILED DESCRIPTION OF EMBODIMENTS OF THE INVENTION

Figure 1:
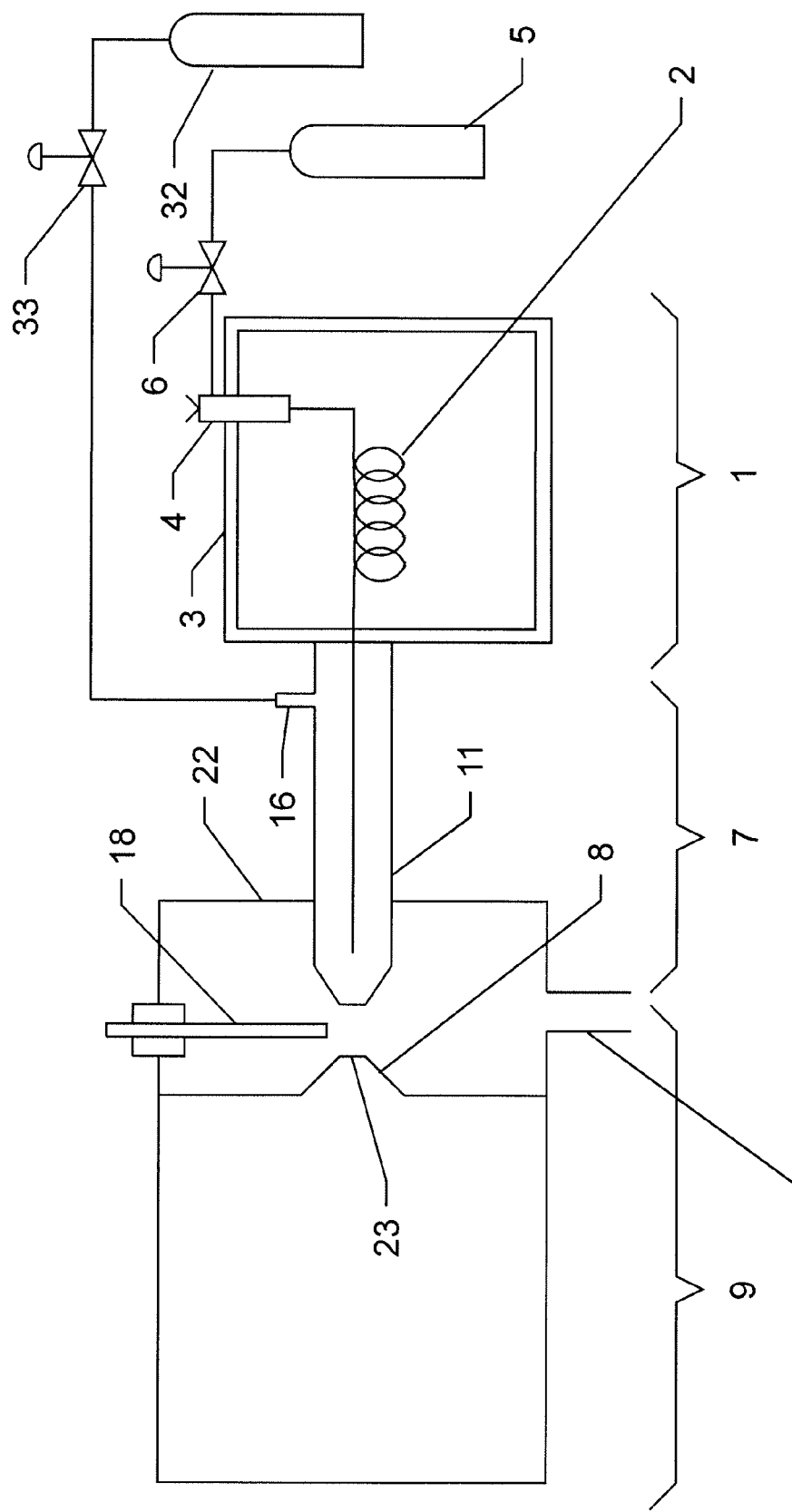
FIG. 1 is a schematic drawing of a GCMS instrument according to one embodiment of the invention.

An embodiment of the invention comprising a gas chromatograph and a mass spectrometer is shown in FIG. 1. A gas chromatograph 1 comprises a capillary column 2 inside a temperature controlled oven 3. Analyte is introduced on to the column 2 through a sample injector 4 into a flow of a first gas from a reservoir 5. A flow controller 6 is provided to maintain a constant flow of the first gas, which may conveniently comprise helium. A flow of about 1 ml/minute would be suitable for many capillary GC columns. The column 2 is a coil of metal or glass capillary tubing, typically 250 µm internal diameter and 350 µm outside diameter, internally coated with a stationary phase suitable for effecting separation of different chemical components comprised in the analyte. The effluent from the column 2, comprising analyte molecules in a flow of the first gas at a pressure approximately equal to or slightly greater than atmospheric pressure, passes into an interface device generally indicated at 7 and which is described in detail below.

Gas and analyte molecules emerge from the interface device 7 and are sampled through a small orifice 23 in a sampling cone 8 which comprise the entrance to a mass spectrometer generally indicated by 9. The mass spectrometer 9 is any mass spectrometer capable of analyzing ions present in a gas at substantially atmospheric pressure, and may comprise one or more ion traps and/or quadrupole, magnetic sector, electrostatic sector, or time-of-flight analysers. The mass spectrometer 9 may further comprise one or more collision cells, reaction cells or mobility separation stages for separating or fragmenting analyte ions or for reacting them with another species such as neutral molecules, ions of polarity opposite to those of the analyte ions, or electrons. Preferably, these cells are disposed ahead of or between the analysers or traps and comprise ion guides or other ion transmission devices to assist transmission of ions through the cell. The mass spectrometer 9 may further comprise one or more pressure reduction stages for progressively reducing the pressure, disposed between the sampling cone 8 and the first of the analysers or ion traps. These pressure reduction stages comprise ion guides for efficiently transmitting ions through each stage and from one stage to the next. Ion guides incorporated in the mass spectrometer comprise multipole rod sets, such as quadrupoles, hexapoles, or octupoles, or ring sets or linear or quadrupole ion traps. Mass spectrometers comprising these various combinations of components are known in the art and need not be described in detail. Selection of a mass spectrometer suitable for use with the invention will be made with knowledge of the nature of the analyte molecules and the information required from the analyses.

Figure 2:
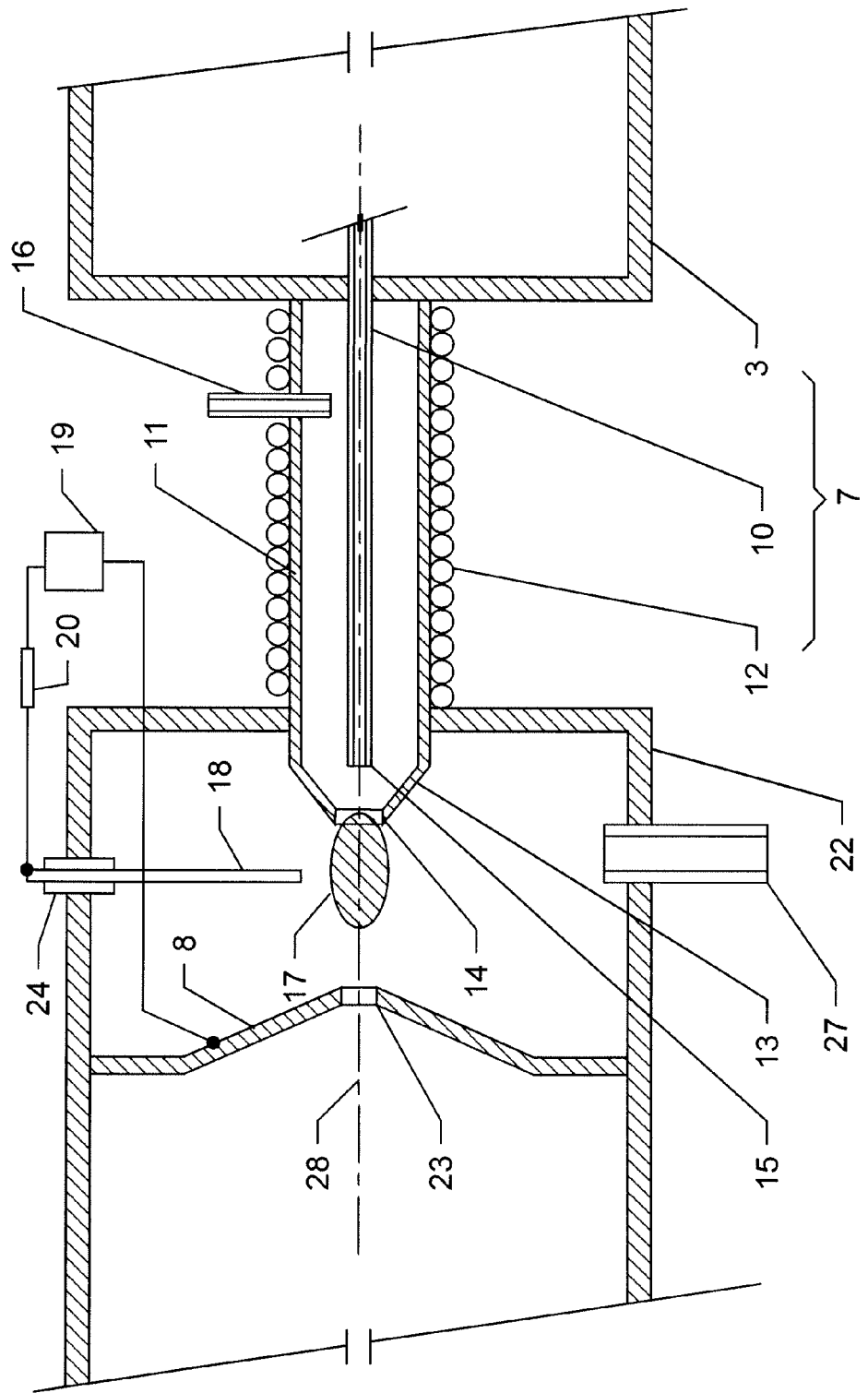
FIG. 2 is a drawing of one arrangement of part of the instrument shown in FIG. 1 in which APCI is used.

An embodiment of the interface device 7 is shown in FIG. 2. The inlet tube 10 is either integral with, or is connected to, the outlet of the column 2. The inlet tube 10 (or the column 2) extends through the wall of the oven 3 towards the sampling cone 8 of the mass spectrometer 9, as shown. It is surrounded by a sheath tube 11, which is heated by a heater 12. Preferably, the sheath tube 11 is a metal or metal alloy, such as stainless steel, or glass, or quartz, or plastic, having an about 2 mm inside diameter and the heater 12 may be a coiled resistance wire or tape heater, similar to those used for conventional GCMS interfaces. The heater 12 is capable of maintaining the temperature of the inlet tube 10 sufficiently high to prevent loss of analyte molecules as they travel through the tube. The necessary temperature is dependent on the nature of the analyte molecules, but may typically be in the range 100-300° C., as in the case of conventional GCMS apparatus.

The sheath tube 11 has a second exit 14 and an end portion 13 which narrows to a smaller diameter towards the second exit 14 downstream of the first exit 15 of the inlet tube 10, as shown in FIG. 2. A supply of a second gas (typically nitrogen or another inert gas such as argon) from a reservoir 32 (FIG. 1) is connected to a sheath tube inlet 16 via a flow controller 33 (FIG. 1). The second gas flows in the annular space between the inside of the sheath tube 11 and the exterior of the inlet tube 10 and exits through the small diameter second exit 14 of the sheath tube 11. The end portion 13 of the sheath tube 11 is preferred be part-conical, but other tapered forms can be employed if desired. Such geometry directs the flow of second gas towards the axis 28 of the inlet tube 10 and the sheath tube 11 as it leaves the second exit 14.

The first gas and analyte molecules comprised in it flow through the inlet tube 10 from the gas-chromatographic column 2 and are discharged from the first exit 15 of the inlet tube 10 into an ionization region 17. The inventor believes that the second gas leaving sheath tube 11 through the second exit 14 exerts an aerodynamic focusing effect on the flow of first gas as it leaves the first exit 15 of the inlet tube 10. This aerodynamic focusing effect limits the expansion of the first gas and analyte molecules as they leave inlet tube 10 and reduces the volume of the ionization region 17 in comparison that which it might occupy in the absence of the second gas. Consequently, the concentration of analyte molecules in the ionization region 17 is increased.

In order for aerodynamic focusing to be obtained, the linear flow velocity of the second gas as it emerges from the second exit 14 of the end portion 13 of the sheath tube 11 is preferably greater than the linear flow velocity of the first gas from the first exit 15 of the inlet tube 10. With the tube dimensions specified above, the flow of second gas is, preferably, at least ten times greater than the flow of first gas. Therefore a flow of about 10-20 ml/minute of the second gas would be appropriate when the flow of first gas from the chromatographic column is about 1 ml/minute.

Figure 5:
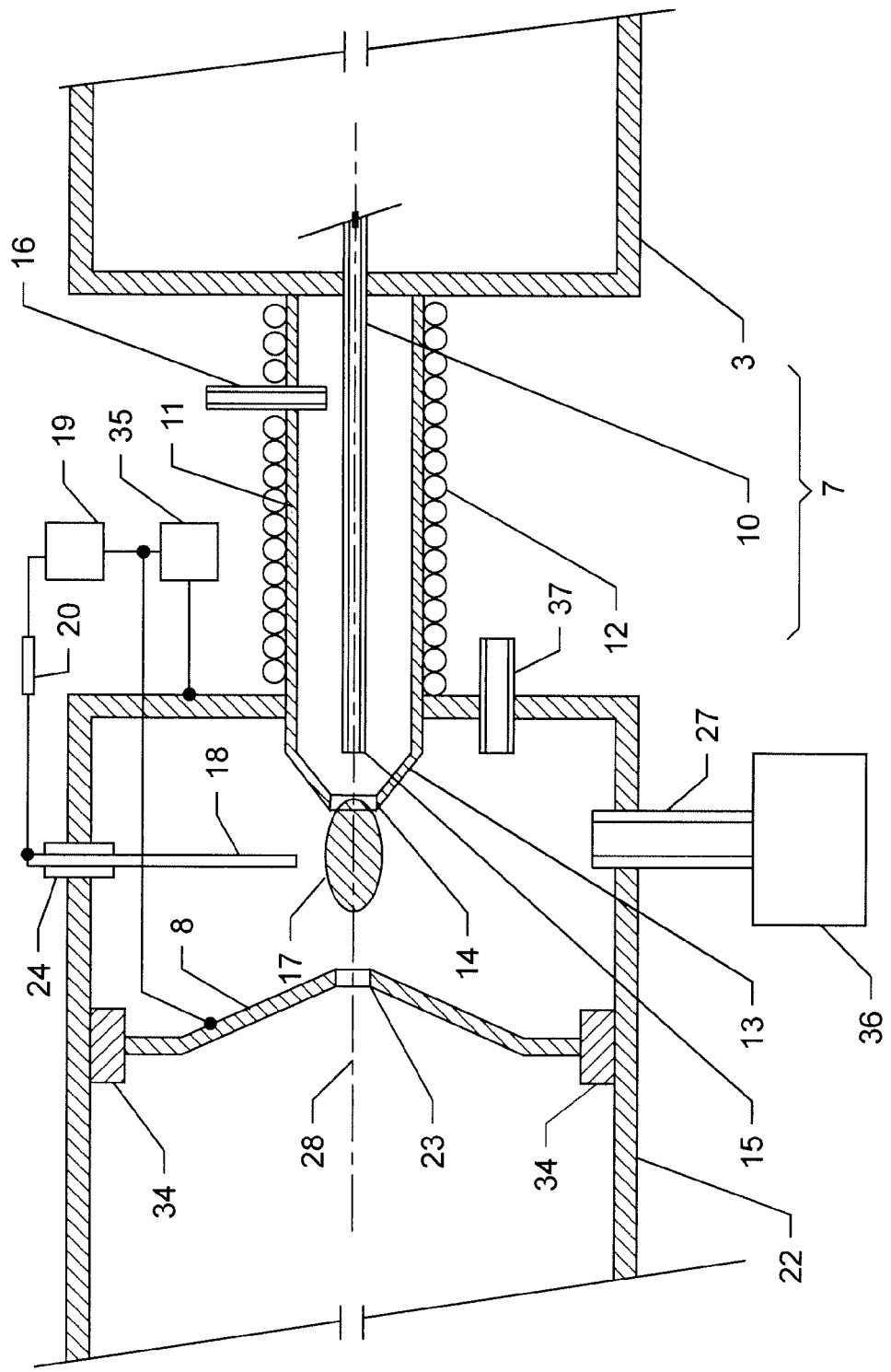
FIG. 5 is a drawing of another embodiment of part of the instrument shown in FIG. 1 in which APCI is used.

Analyte molecules present in the ionization region 17 are ionized through atmospheric pressure chemical ionization. In the embodiment shown in FIG. 2, the pressure in the ionization region 17 is equal to or slightly greater than atmospheric pressure, and ionization may be effected through a corona discharge established by application of a suitable electrical potential difference between an electrode 18 and at least the sampling cone 8 of the mass spectrometer 9. A power supply 19 connected to the electrode 18 via a current limiting resistor 20 may be employed to provide this potential difference. Apparatus for ionizing molecules by atmospheric pressure chemical ionization using a corona discharge is well known in the art and need not be described in detail. In the FIG. 2 embodiment, the electrode 18 is disposed downstream of the second exit 14. A housing 22 comprising a vent 27 surrounds the ionization region 17 and the corona discharge. The electrode 18 is mounted through the wall of the housing 22 in an insulator 24. If housing 22 is electrically conductive, it may be connected to the sampling cone 8 of the mass spectrometer 9 and serve as a counter electrode to the corona electrode 18, in addition to the cone 8 itself. Alternatively, the sample cone 8 is insulated from the housing 22 by an insulator 34 to allow it to be maintained at a potential different from that at which the housing 22 is maintained (usually ground potential). A power supply 35 is connected, as shown in FIG. 5, for this purpose. It has been found that maintaining a potential difference of between 20 and 100 volts between the cone 8 and the housing 22 is advantageous in some circumstances, but other potential differences may be used if desired. The sampling cone 8 is maintained at a positive potential relative to the housing 22 when positive ions are to be analysed, and at a negative potential when negative ions are to be analysed.

The vent 27 discharges to atmospheric pressure so that the pressure inside the housing 22 is equal to or slightly greater than atmospheric pressure. However, it is within the scope of the invention for a pressure lower than atmospheric to be used, for example by connecting a pump 36 to the vent 27, as shown in FIG. 5.

In such a case the pressure in the ionization region 17 is greater than 300 torr but less than atmospheric pressure. A vent 37, typically connected to a source of the second gas, is provided to prevent the pressure in the ionization region 17 falling too much when the pump 36 is operating.

The pressure in the ionization region 17 should be greater than 300 torr and may preferably be between about 650 torr and 850 torr. It may be maintained approximately equal to atmospheric pressure, or slightly above or below atmospheric pressure.

Figure 3:
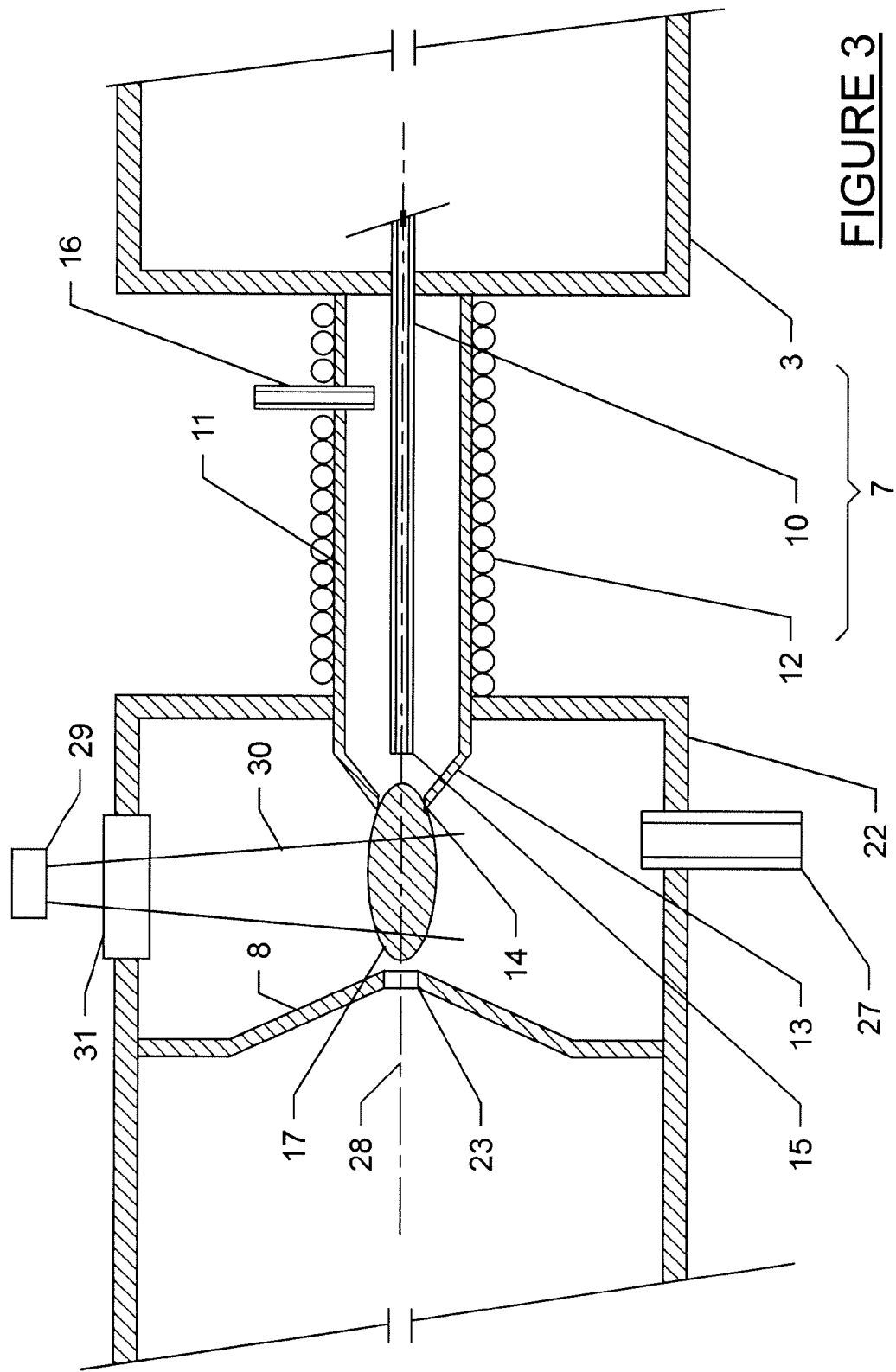
FIG. 3 is a drawing of another arrangement of part of the instrument shown in FIG. 1 in which APPI is used.

Analyte molecules may alternatively be ionized in the ionization region 17 by atmospheric pressure photoionization (APPI). Such an embodiment is shown in FIG. 3. It differs chiefly from the APCI embodiment shown in FIG. 2 in that the electrode 18 is replaced by a UV light source 29 which generates beam of photons 30 which intersects the ionization region 17 in order to ionize at least some of the analyte molecules by APPI. The UV light source 29 may be a UV lamp or a UV laser and a UV transparent window 31 may be provided in the housing 22 to allow passage of the beam 30.

Ions generated in the ionization region 17 by APCI or APPI pass through an orifice 23 in the sampling cone 8 and are subsequently analysed by the mass spectrometer 9, as explained in general terms above. Because the analyte ions are confined in the ionization region 17 in a smaller volume than they would be in the absence of the aerodynamic focusing, the number of ions which are able to enter the orifice 23 is increased. This in turn results in an increased sensitivity of the gas-chromatograph mass spectrometer system in comparison with a similar prior system which did not comprise the aerodynamic focusing.

Figure 4:
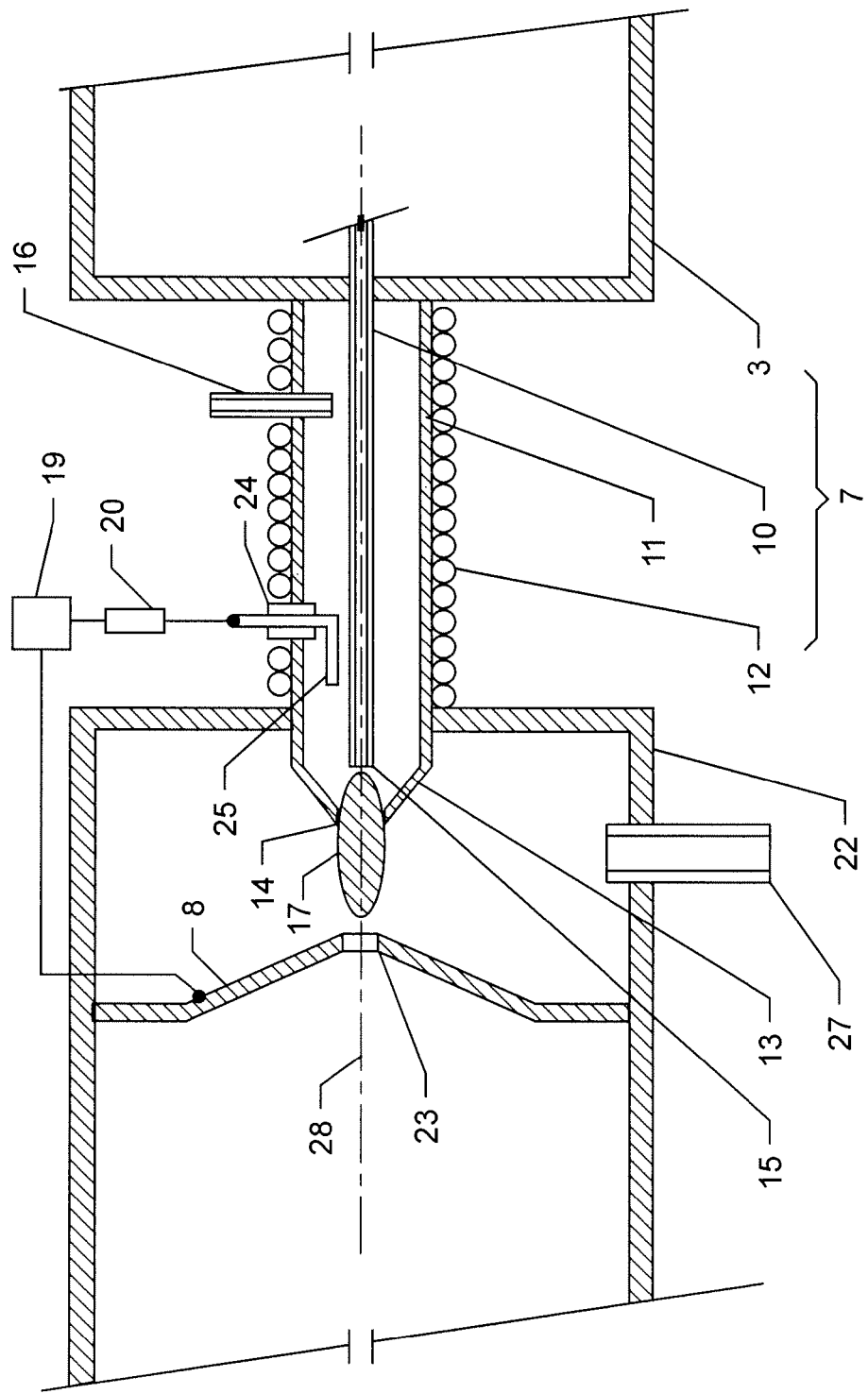
FIG. 4 is a drawing of an alternative arrangement of part of the instrument shown in FIG. 1 in which APCI is used.

Another embodiment of the invention is shown in FIG. 4. This embodiment differs from the FIG. 2 embodiment primarily in the location of the corona electrode 25 which replaces the electrode 18 of FIG. 2. Electrode 25 is disposed in the space between the sheath tube 11 and the inlet tube 10, upstream of the end portion 13 of the sheath tube 11. Electrode 25 is fitted through an insulator 26 in the wall of the sheath tube 11. In this embodiment, ions are generated from molecules of the second gas in the corona discharge inside the sheath tube 11, and carried in the flow of the second gas into the ionization region 17. Here they may react with analyte molecules entering the ionization region 17 from the first exit 15 of the inlet tube 10. Aerodynamic focusing occurs at the second exit 14 of the sheath tube 11. Second exit 14 is of smaller diameter than the remainder of the sheath tube 11, and the end portion 13 of the sheath tube 11 may be profiled towards the second exit 14 as it is in the case of the FIG. 2 embodiment.

In the FIG. 4 embodiment, the ionization region 17 extends farther into the sheath tube 11 than it does in the case of the FIG. 2 embodiment, so that analyte ions are formed within the heated portion of the sheath tube 11 by reaction with reagent ions generated close to the electrode 25. This arrangement reduces the losses of analyte on the surfaces of the sheath tube and other cooler portions of the apparatus. Further, the absence of the electrode 18 (FIG. 2) from the region between the sampling cone 8 and the exit 14 of the sheath tube 11 allows the distance between the orifice 23 and the exit 14 to be reduced, leading to a greater number of analyte ions entering the mass spectrometer 9, and greater sensitivity.

Thus, the present invention has been described with respect to the best mode of making and using it with the understanding that the invention as described can be modified and altered without departing from the teaching herein. Therefore, the invention should not be limited to the preceding description but should encompass the subject matter of the claims that follow and their equivalents.

The invention claimed is:

1. Apparatus for ionizing analyte molecules comprised in a flow of a first gas, said apparatus comprising:
    a) an inlet tube having a first exit through which said first gas is discharged into an ionization region downstream of said first exit at a first linear velocity;
    b) a sheath tube disposed around said inlet tube to define a substantially annular space between the exterior of said inlet tube and the interior of said sheath tube, said sheath tube comprising a second exit downstream of said first exit;
    c) means for causing a flow of a second gas to flow through said substantially annular space through said second exit at a second linear velocity, higher than said first linear velocity; and
    d) means for ionizing at least some of said analyte molecules in said ionization region, wherein said means for ionizing comprises a corona discharge generated using a corona electrode positioned downstream of both said first and second exits;
    wherein, downstream of said first exit, said sheath tube narrows to direct the flow of said second gas around said ionization region and to limit its volume.

2. Apparatus as claimed in claim 1 wherein said inlet tube and said sheath tube are concentrically disposed about an axis.

3. Apparatus as claimed in claim 2 wherein said sheath tube is formed so that its cross sectional area decreases steadily beyond said first exit so that the flow of the second gas as it leaves said second exit is directed towards said axis.

4. Apparatus as claimed in claim 1 wherein said first gas is discharged into said ionization region at a pressure greater than 300 torr.

5. Apparatus as claimed in claim 4 wherein said analyte molecules are ionized by atmospheric pressure chemical ionization (APCI) processes using said corona discharge.

6. Apparatus as claimed in claim 1 wherein said first gas is discharged into said ionization region at a pressure between 650 and 850 torr.

7. Apparatus as claimed in claim 1 wherein said first gas is discharged into said ionization region at approximately atmospheric pressure.

8. Apparatus as claimed in claim 1 further comprising a gas chromatograph and a chromatographic column, and wherein said flow of a first gas comprises effluent from said gas chromatographic column.

9. Apparatus as claimed in claim 8 further comprising a mass spectrometer having an entrance orifice disposed to receive ions formed in said ionization region.

10. Apparatus as claimed in claim 1 wherein said inlet tube comprises a capillary tube.

11. Apparatus as claim 1 wherein said sheath tube is heated.

12. Apparatus as claimed in claim 1 further comprising a mass spectrometer having an entrance orifice disposed to receive ions formed in said ionization region.

13. Apparatus for ionizing analyte molecules comprised in a flow of a first gas, said apparatus comprising:
    a) an inlet tube having a first exit through which said first gas is discharged into an ionization region downstream of said first exit at a first linear velocity;
    b) a sheath tube disposed around said inlet tube to define a substantially annular space between the exterior of said inlet tube and the interior of said sheath tube, said sheath tube comprising a second exit downstream of said first exit;
    c) means for causing a flow of a second gas to flow through said substantially annular space through said second exit at a second linear velocity, higher than said first linear velocity; and
    d) means for ionizing at least some of said analyte molecules in said ionization region, wherein said means for ionizing comprises a corona discharge generated using a corona electrode disposed upstream of said first exit in the space between said inlet tube and said sheath tube;
    wherein, downstream of said first exit, said sheath tube narrows to direct the flow of said second gas around said ionization region and to limit its volume.

14. A method of ionizing analyte molecules comprised in a flow of a first gas, said method comprising:
    a) passing said first gas through an inlet tube having a first exit and discharging it at a first linear velocity through said first exit into an ionization region downstream of said first exit;
    b) passing a second gas through a substantially annular space between the exterior of said inlet tube and the interior of a sheath tube having a second exit and which is disposed around said inlet tube, and discharging said second gas at a second linear velocity, greater than said first linear velocity, through said second exit downstream of said first exit; and
    c) ionizing at least some of said analyte molecules in said ionization region, wherein said at least some analyte molecules are ionized using a corona discharge generated using a corona electrode positioned downstream of both said first and second exits;
    wherein said second gas is directed through said second exit towards the axis of said sheath tube to surround said ionization region and to limit its volume.

15. A method as claimed in claim 14 wherein said first gas is discharged into the ionization region at a pressure greater than 300 torr.

16. A method as claimed in claim 14 wherein said first gas is discharged into the ionization region at a pressure between 650 and 850 torr.

17. A method as claimed in claim 14 wherein said first gas is discharged into the ionization region at approximately atmospheric pressure.

18. A method as claimed in claim 14 wherein said at least some analyte molecules are ionized by APCI using said corona discharge.

19. A method as claimed in claim 14 further comprising introducing analyte molecules into said first gas, passing the resultant gas through a gas chromatographic column to separate in time different analyte molecules, and passing the effluent from said chromatographic column into said inlet tube.

20. A method as claimed in claim 14 wherein ions generated in the ionization region are passed into a mass spectrometer for mass analysis.

21. A method as claimed in claim 14 wherein said second gas is nitrogen.

22. A method as claimed in claim 14 wherein the flow rate of said second gas is at least ten times the flow rate of said first gas.

23. A method of ionizing analyte molecules comprised in a flow of a first gas, said method comprising:

a) passing said first gas through an inlet tube having a first exit and discharging it at a first linear velocity through said first exit into an ionization region downstream of said first exit;

b) passing a second gas through a substantially annular space between the exterior of said inlet tube and the interior of a sheath tube having a second exit and which is disposed around said inlet tube, and discharging said second gas at a second linear velocity, greater than said first linear velocity, through said second exit downstream of said first exit; and c) ionizing at least some of said analyte molecules in said ionization region, wherein said at least some analyte molecules are ionized using a corona discharge generated using a corona electrode disposed upstream of said first exit in the space between said inlet tube and said sheath tube;

wherein said second gas is directed through said second exit towards the axis of said sheath tube to surround said ionization region and to limit its volume.

* * * * *